(12) United States Patent
Kokish

(10) Patent No.: US 6,651,478 B1
(45) Date of Patent: *Nov. 25, 2003

(54) ASSEMBLY FOR CRIMPING AN INTRALUMINAL DEVICE OR MEASURING THE RADIAL STRENGTH OF THE INTRALUMINAL DEVICE AND METHOD OF USE

(75) Inventor: Arkady Kokish, Los Gatos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 7 days.

This patent is subject to a terminal disclaimer.

(21) Appl. No.: 09/997,783

(22) Filed: Nov. 28, 2001

Related U.S. Application Data

(63) Continuation-in-part of application No. 09/636,093, filed on Aug. 10, 2000, now Pat. No. 6,568,235.

(51) Int. Cl.[7] ............................................. B21D 41/04
(52) U.S. Cl. ............................ 72/402; 29/283.5; 606/1
(58) Field of Search .............................. 72/402; 29/237, 29/282, 283.5; 606/1

(56) References Cited

U.S. PATENT DOCUMENTS

| | | | |
|---|---|---|---|
| 141,992 A | 8/1873 | Carr | |
| 430,928 A | 6/1890 | Doty | |
| 579,214 A | 3/1897 | Adams | |
| 696,289 A | 3/1902 | Williams | |
| 852,290 A | 4/1907 | Neal | |
| 915,184 A | 3/1909 | Keirn | |
| 1,045,886 A | 12/1912 | Reay | |
| 1,230,561 A | 6/1917 | Chige | |
| 1,268,171 A | 6/1918 | Spaulding | |
| 1,785,261 A | 5/1930 | Leland | |
| 2,452,857 A | 11/1948 | Mesaros | |
| 2,465,433 A | 3/1949 | Doniger | |
| 2,553,479 A | 5/1951 | Schmarje et al. | |
| 2,964,088 A | 12/1960 | Erath | |
| 3,439,519 A | 4/1969 | Gerding | |
| 3,496,684 A | 2/1970 | Banning et al. | |
| 3,568,495 A | 3/1971 | Duffield et al. | |
| 3,619,885 A | 11/1971 | Dischler | |
| 3,695,087 A | * 10/1972 | Tuberman | 72/402 |

(List continued on next page.)

FOREIGN PATENT DOCUMENTS

| | | |
|---|---|---|
| CA | 2211694 | 2/1998 |
| DE | 464004 | 7/1928 |
| DE | 297 14857 U1 | 11/1997 |

(List continued on next page.)

OTHER PUBLICATIONS

U.S. patent application Ser. No. 09/928,877, filed Sep. 12, 1997.

U.S. patent application Ser. No. 09/032,472, filed Feb. 26, 1998.

(List continued on next page.)

Primary Examiner—Daniel C. Crane
(74) Attorney, Agent, or Firm—Fulwider Patton Lee & Utecht, LLP

(57) ABSTRACT

An assembly is provided which can crimp or compress an intraluminal device or measure the radial strength of an intraluminal device. The device includes a stationary disk and a drive disk for imparting movement to a number of wedges attached to linear sliders on the stationary disk. As rotational movement is imparted by the drive disk to the wedges, the wedges move in a linear direction to form a crimping motion for use in crimping an intravascular intraluminal device onto a catheter or a mandrel. Alternatively, the same motion of the wedges is used to measure the radial strength of an intraluminal device.

73 Claims, 11 Drawing Sheets

U.S. PATENT DOCUMENTS

| | | |
|---|---|---|
| 3,898,897 A | 8/1975 | Jauhiainen |
| 4,043,172 A | 8/1977 | Schmittou |
| 4,070,745 A | 1/1978 | Schimmelman |
| 4,107,964 A | 8/1978 | Smith |
| 4,215,871 A | 8/1980 | Hirsch et al. |
| 4,353,240 A | 10/1982 | Undin et al. |
| 4,373,923 A | 2/1983 | Kilwin |
| 4,379,397 A | 4/1983 | Langr |
| 4,455,854 A | 6/1984 | Ermolovich et al. |
| 4,468,224 A | 8/1984 | Enzmann et al. |
| 4,576,142 A | 3/1986 | Schiff |
| 4,606,347 A | 8/1986 | Fogarty et al. |
| 4,644,936 A | 2/1987 | Schiff |
| 4,681,092 A | 7/1987 | Cho et al. |
| 4,697,573 A | 10/1987 | Schiff |
| 4,703,546 A | 11/1987 | Gilbert |
| 4,786,271 A | 11/1988 | Menn |
| 4,838,264 A | 6/1989 | Bremer et al. |
| 4,864,924 A | 9/1989 | Storace |
| 4,901,707 A | 2/1990 | Schiff |
| 4,907,336 A | 3/1990 | Gianturco |
| 4,961,291 A | 10/1990 | Lagassee |
| 4,987,722 A | 1/1991 | Koebbeman |
| 5,132,066 A | 7/1992 | Charlesworth et al. |
| 5,133,732 A | 7/1992 | Wiktor |
| 5,183,085 A | 2/1993 | Timmermans |
| 5,189,786 A | 3/1993 | Ishikawa et al. |
| 5,195,539 A | 3/1993 | Dyrud et al. |
| 5,207,960 A | 5/1993 | Moret de Rocheprise |
| 5,209,143 A | 5/1993 | Sweet |
| 5,209,799 A | 5/1993 | Vigil |
| 5,217,434 A | 6/1993 | Arney |
| 5,263,969 A | 11/1993 | Phillips |
| 5,336,234 A | 8/1994 | Vigil et al. |
| 5,352,197 A | 10/1994 | Hammersmark et al. |
| 5,437,083 A | 8/1995 | Williams et al. |
| 5,456,667 A | 10/1995 | Ham et al. |
| 5,458,615 A | 10/1995 | Klemm et al. |
| 5,465,716 A | 11/1995 | Avitall |
| 5,476,505 A | 12/1995 | Limon |
| 5,540,124 A | 7/1996 | Srhoj |
| 5,546,646 A | 8/1996 | Williams et al. |
| 5,626,474 A | 5/1997 | Kukla et al. |
| 5,626,604 A | 5/1997 | Cottone, Jr. |
| 5,628,754 A | 5/1997 | Shevlin et al. |
| 5,630,830 A | 5/1997 | Verbeek |
| 5,653,691 A | 8/1997 | Rupp et al. |
| 5,658,181 A | 8/1997 | Brown, II |
| 5,672,169 A | 9/1997 | Verbeek |
| 5,693,066 A | 12/1997 | Rupp et al. |
| 5,695,515 A | 12/1997 | Orejola |
| 5,715,723 A | 2/1998 | Owens |
| 5,725,519 A | 3/1998 | Penner et al. |
| 5,738,674 A | 4/1998 | Williams et al. |
| 5,746,764 A | 5/1998 | Green et al. |
| 5,759,474 A | 6/1998 | Rupp et al. |
| 5,782,855 A | 7/1998 | Lau et al. |
| 5,782,903 A | 7/1998 | Wiktor |
| 5,783,227 A | 7/1998 | Dunham |
| 5,785,715 A | 7/1998 | Schatz |
| 5,787,572 A | 8/1998 | Toms et al. |
| 5,795,289 A | 8/1998 | Wyttenbach |
| 5,810,838 A | 9/1998 | Solar |
| 5,810,871 A | 9/1998 | Tuckey et al. |
| 5,810,873 A | 9/1998 | Morales |
| 5,836,952 A | 11/1998 | Davis et al. |
| 5,860,966 A | 1/1999 | Tower |
| 5,893,852 A | 4/1999 | Morales |
| 5,893,867 A | 4/1999 | Bagaoisan et al. |
| 5,911,452 A | 6/1999 | Yan |
| 5,920,975 A | 7/1999 | Morales |
| 5,931,851 A | 8/1999 | Morales |
| 5,938,696 A | 8/1999 | Goicoechea et al. |
| 5,944,735 A | 8/1999 | Green et al. |
| 5,947,993 A | 9/1999 | Morales |
| 5,948,191 A | 9/1999 | Solovay |
| 5,951,569 A | 9/1999 | Tuckey et al. |
| 5,972,016 A | 10/1999 | Morales |
| 5,974,652 A | 11/1999 | Kimes et al. |
| 6,009,614 A | 1/2000 | Morales |
| 6,024,737 A | 2/2000 | Morales |
| 6,051,002 A | 4/2000 | Morales |
| 6,063,102 A | 5/2000 | Morales |
| 6,082,990 A | 7/2000 | Jackson et al. |
| 6,092,273 A | 7/2000 | Villareal |
| 6,108,886 A | 8/2000 | Kimes et al. |
| 6,125,523 A | 10/2000 | Brown et al. |
| 2001/0001890 A1 | 5/2001 | Austin |

FOREIGN PATENT DOCUMENTS

| | | |
|---|---|---|
| EP | 0 303 889 B1 | 6/1993 |
| EP | 0 562 478 B1 | 12/1994 |
| EP | 0 630 623 A2 | 12/1994 |
| EP | 0 630 623 A3 | 12/1994 |
| EP | 0 697 226 A1 | 2/1996 |
| EP | 0 826 346 A1 | 3/1998 |
| EP | 0 873 731 A1 | 10/1998 |
| EP | 0 938 877 A2 | 9/1999 |
| EP | 0 938 880 A2 | 9/1999 |
| EP | 0 938 880 A3 | 11/1999 |
| FR | 975797 | 3/1951 |
| GB | 159065 | 2/1921 |
| GB | 2 088 811 A | 6/1982 |
| JP | 02180275 | 7/1990 |
| JP | 445187 | 7/1992 |
| JP | 7-47135 | 3/1995 |
| JP | 7-67967 | 3/1995 |
| JP | 11-19230 | 1/1999 |
| WO | WO 93/06780 | 4/1993 |
| WO | WO 97/09946 | 3/1997 |
| WO | WO 98/14120 | 4/1998 |
| WO | WO 98/19633 | 5/1998 |

OTHER PUBLICATIONS

U.S. patent application Ser. No. 09/069,010, filed Apr. 28, 1998.

U.S. patent application Ser. No. 09/401,705, filed Sep. 23, 1999.

U.S. patent application Ser. No. 09/475,694, filed Dec. 30, 1999.

User Manual *Tominator©* Stent Crimping Equipment (Undated).;

Bard XT Stent Brochure: *The eXTraordinary Stent* (Undated).

*Corporate Profile–Machine Solutions, Inc.*, Reprinted from *European Medical Device Manufacturer*, Jul./Aug. 2000 ●Copyright © 2000 Canon Communications LLC.

MSI Equipment pages, www.machinesolutions.org, Copyright © 2002 Machine Solutions, Inc.

* cited by examiner

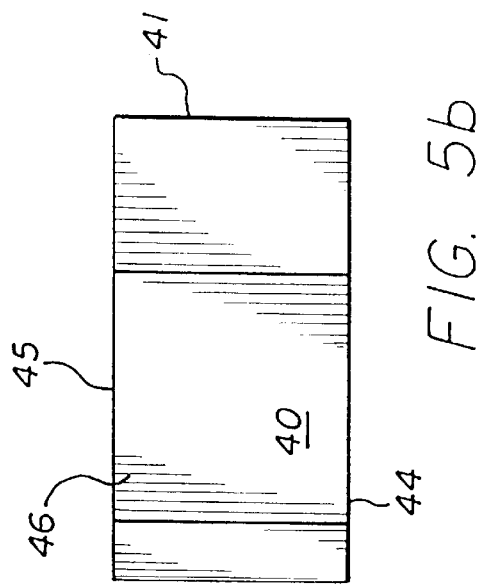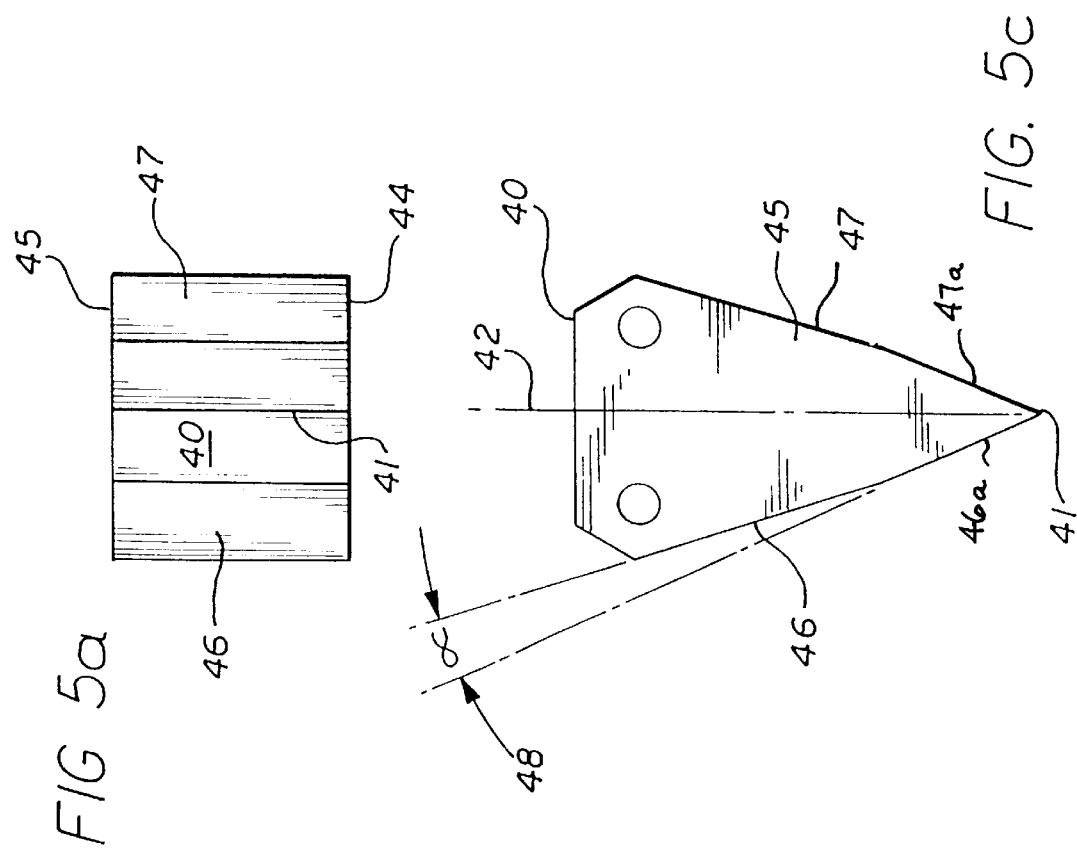

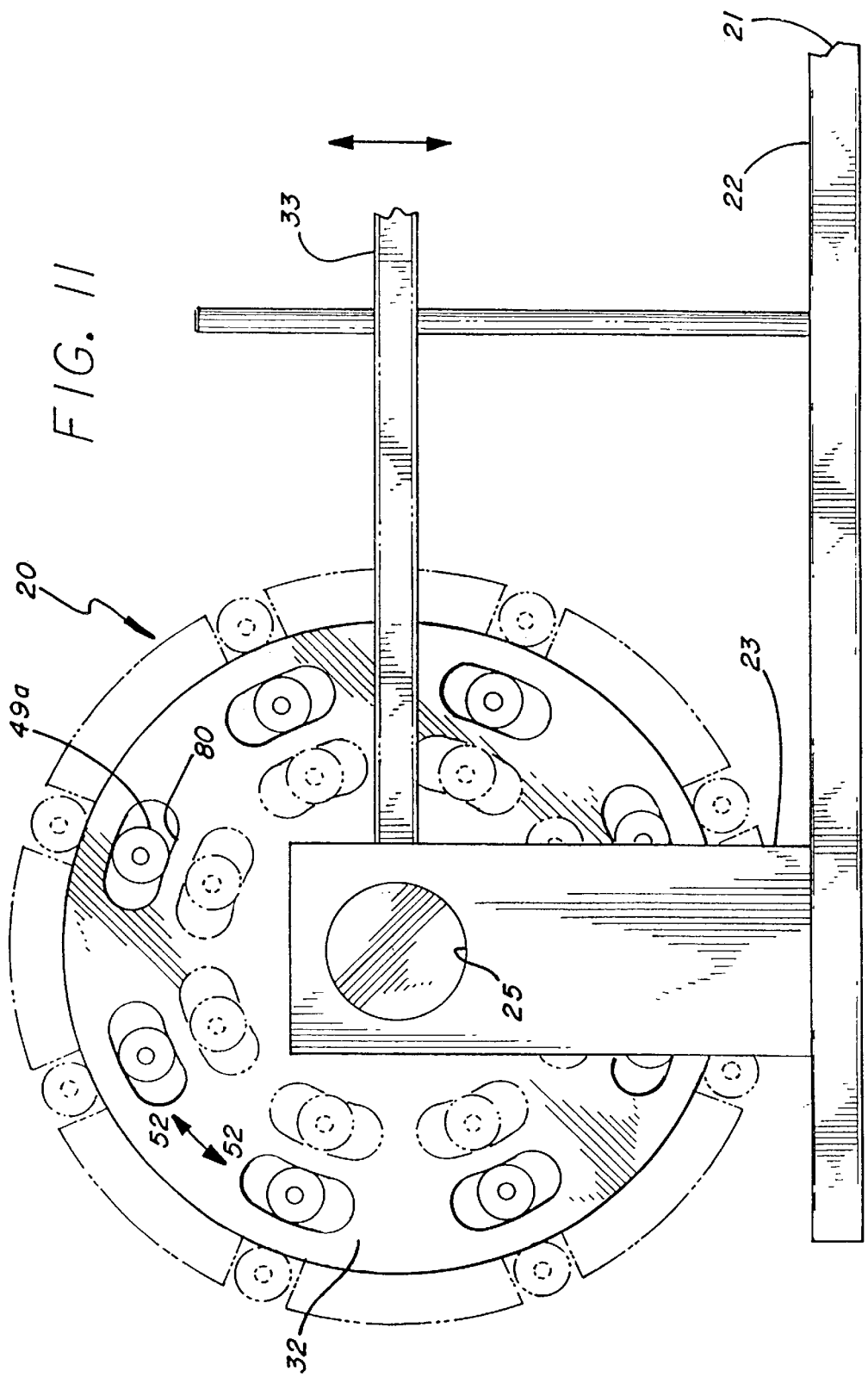

ASSEMBLY FOR CRIMPING AN INTRALUMINAL DEVICE OR MEASURING THE RADIAL STRENGTH OF THE INTRALUMINAL DEVICE AND METHOD OF USE

This is a continuation of Ser. No. 09/636,093, filed Aug. 10, 2000, now U.S. Pat. No. 6,568,235.

BACKGROUND OF THE INVENTION

The present invention relates to an apparatus for loading an intraluminal device, such as a stent or an embolic device such as a filter, onto the distal end of a catheter assembly similar to those used, for example, in percutaneous transluminal coronary angioplasty (PTCA) procedures or in percutaneous transluminal angioplasty (PTA) procedures. The present invention device is useful in crimping balloon-expandable stents and self-expanding stents.

In typical PTCA procedures, a guiding catheter is percutaneously introduced into the cardiovascular system of a patient through the brachial or femoral arteries and advanced through the vasculature until the distal end of the guiding catheter is in the ostium of the aorta leading to the coronary arteries. A guide wire and a dilatation catheter having a balloon on the distal end are introduced through the guiding catheter with the guide wire sliding within the dilatation catheter. The guide wire is first advanced out of the guiding catheter into the patient's coronary vasculature and the dilatation catheter is advanced over the previously advanced guide wire until the dilatation balloon is properly positioned across the arterial lesion. Once in position across the lesion, a flexible and expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, restenosis of the artery may develop at or near the treatment area, which may require another angioplasty procedure, a surgical bypass operation, or some other method of repairing or strengthening the area. To reduce the likelihood of the development of restenosis and to strengthen the area, a physician can implant an intravascular prosthesis for maintaining vascular patency, commonly known as a stent, inside the artery at the treated area. The stent is transported in its low profile delivery diameter through the patient's vasculature. At the deployment site, the stent is expanded to a larger diameter, often by inflating the balloon portion of the catheter. The stent also may be of the self-expanding type.

Since the catheter and stent travel through the patient's vasculature, and typically through the coronary arteries, the stent must have a small delivery diameter and must be firmly attached to the catheter until the physician is ready to implant it. Thus, the stent must be loaded onto the catheter so that it does not interfere with delivery, and it must not come off the catheter until it is implanted.

In procedures where the stent is placed over the balloon portion of the catheter, it is necessary to crimp the stent onto the balloon portion to reduce its diameter and to prevent it from sliding off the catheter when the catheter is advanced through the patient's vasculature. Non-uniform crimping can result in sharp edges being formed along the now uneven surface of the crimped stent. Furthermore, non-uniform stent crimping may not achieve the desired minimal profile for the stent and catheter assembly. Where the stent is not reliably crimped onto the catheter, the stent may slide off the catheter and into the patient's vasculature prematurely as a loose foreign body, possibly causing blood clots in the vasculature, including thrombosis. Therefore, it is important to ensure the proper crimping of a stent onto a catheter in a uniform and reliable manner.

This crimping is sometimes done by hand, which can be unsatisfactory due to the uneven application of force resulting in non-uniform crimps. In addition, it is difficult to visually judge when a uniform and reliable crimp has been applied.

Some self-expanding stents are difficult to load by hand into a delivery device such as a catheter. Self-expanding stents typically are compressed or crimped to a small diameter and then inserted into a delivery catheter where the stent remains until it is pushed out and expands into the vessel. Further, the more the stent is handled the higher the likelihood of human error, which would be antithetical to a properly crimped stent. Accordingly, there is a need in the art for a device for reliably crimping or compressing a self-expanding stent and inserting it into a catheter.

There have been attempts at devising a tool for crimping a stent onto a balloon delivery catheter. An example of such a tool comprises a series of plates having substantially flat and parallel surfaces that move in a rectilinear fashion with respect to each other. A stent carrying catheter is disposed between these surfaces, which surfaces crimp the stent onto the outside of the catheter by their relative motion and applied pressure. The plates have multiple degrees of freedom and may have force-indicating transducers to measure and indicate the force applied to the catheter during crimping of the stent.

Another stent loading tool design is comprised of a tubular member housing a bladder. The tubular member and bladder are constructed to hold a stent that is to be crimped onto a balloon catheter assembly. Upon placement of the stent over the balloon portion of the catheter, a valve in the loading tool is activated to inflate the bladder. The bladder compresses the stent radially inward to a reduced diameter onto the balloon portion of the catheter to achieve a snug fit. In this way, the stent is crimped onto the distal end of a balloon catheter with a minimum of human handling. The foregoing stent crimping tools are disclosed in, for example, commonly owned and assigned U.S. Pat. Nos. 5,437,083 and 5,546,646 to Williams et al.

Yet another stent crimping tool is known in the art as the BARD XT, which is actually a stent loader. It is constructed of a tubular body with a ball at one end connected to a plurality of long, thin strips passing through the rigid tubular body. An uncrimped stent is placed over the plurality of long, thin strips, which hold the stent in an expanded state. The balloon portion of a catheter is inserted into the cylindrical space formed by the plurality of strips. When the user pulls on the ball while holding the tubular body against the stent, the strips are slid from beneath the stent and the stent is transferred onto the balloon portion.

Still another conventional stent crimping tool is manufactured by JOHNSON & JOHNSON and appears similar to a hinged nutcracker. Specifically, the tool is comprised of two hand operated levers hinged at one end and gripped in the palm of the hand at the opposite end. A cylindrical opening holding a crimping tube is provided through the mid-portion of the tool to receive therein a stent loaded onto a balloon catheter. The crimping operation is performed by the user squeezing the handle thereby pressing the crimping tube which in turn pinches the stent onto the balloon catheter.

While the prior art devices are suitable for crimping stents onto balloon catheters, they suffer from problems such as non-uniform crimping forces, resulting in non-uniform crimps, and they are unsuitable for use by physicians in a cath lab who desire to crimp the stent onto the balloon catheter.

SUMMARY OF THE INVENTION

The present invention provides for a stent crimping or compressing assembly that is easy to use, and provides a tight and reliable crimped stent onto the distal portion of a stent delivery catheter. Preferably, the stent crimping assembly is used to crimp an expandable stent onto the balloon portion of a catheter, however, the device can be used with self-expanding stents as well. The terms crimping and compressing as used herein are meant to be interchangeable and mean that the diameter of the stent is reduced to some degree. Typically, balloon-expandable stents are known by persons having ordinary skill in the art to be "crimped" onto the balloon portion of a catheter while self-expanding stents are compressed onto a mandrel or sheath and then inserted into a catheter. Also, references to "stent crimping assembly" as used herein is not meant to be limiting since the assembly can be used as a measuring device to accurately measure the radial strength of a stent. Thus, for ease of reference, the device has been referred to throughout as a stent crimping assembly, but it also is used to measure the radial strength of a stent. Further, while reference is made herein to crimping or compressing "stents," the invention can be used with any intraluminal device to reduce the diameter or measure radial strength. Thus, the invention is particularly useful with stents, grafts, tubular prostheses, embolic devices, embolic filters, and embolic retrieval devices.

In one embodiment, the stent crimping assembly includes a stationary disk that has a front face and a rear face that is mounted on a base. The shaft runs through the center of the stationary disk and is attached to a column that is fixed to the base. A drive disk is configured for rotational movement relative to the stationary disk and it also has a front face and a rear face. The drive disk also is attached to a shaft that is coaxial with the shaft attached to the stationary disk. The rear face of the stationary disk is adjacent to and aligned with the front face of the drive disk. A plurality of linear sliders are attached to the front face of the stationary disk. A plurality of wedges, which have a somewhat triangular face, are attached to the linear sliders and to the drive disk. Each wedge has an apex and two exterior edges that define an exterior angle, wherein each wedge is positioned so that it is substantially equidistant from an adjacent wedge. When the drive disk is rotated, the apex of the wedges move in a direction that is perpendicular to the bisect of the exterior angle and as the apex of each wedge continues to move linearly, the apexes of the wedges move from an open position toward a closed position until the apexes come into crimping contact with a stent that has been premounted on the distal portion of a catheter. As the drive disk continues to rotate, more pressure is applied to the apexes of the sliding wedges so that the stent is firmly crimped onto the distal portion of the catheter. At least three wedges and up to N number of wedges can be provided to uniformly crimp the stent onto the distal end of the catheter. In one embodiment, the wedges are mounted on brackets that are positioned between the wedges and the linear sliders, so that the brackets are attached to both the wedges and the linear sliders. The spacing between the wedges can be varied according to the desired application, but it is an important feature of the invention that there is a spacing between the wedges in order to reduce frictional contact. It should be understood by those skilled in the art that the spacing between the wedges is very small and can depend on the number of wedges used and manufacturing tolerances. References to a "disk" herein are not meant to be limiting and, although the disclosed disks are circular, they can be other shapes without departing from the invention (e.g., square, oval, rectangular). If the drive disk is not circular, however, then the roller bearing should be carried in an arcuate slot (see FIG. 11).

An important aspect of the invention is that the apex of each sliding wedge moves in a linear direction that is substantially perpendicular to the bisect of the exterior angle defined by the edges of the wedge. In other words, the wedges are mounted on linear sliders, and even though the drive disk itself has rotational movement, the wedges must move linearly since they are attached to a linear slider.

A roller bearing or similar device can be used to attach the wedge to the drive disk. The roller bearing is used to minimize the frictional engagement between the sliding wedge and the rotational movement of the drive disk. Other similar attachment means can be provided in place of the roller bearing as long as they minimize the frictional engagement between the sliding wedge and the drive disk.

In one embodiment of the invention, the portion of the assembly including the drive disk and the stationary disk can be rotated a preselected number of degrees N to more uniformly crimp the stent. For example, if eight sliding wedges are used to crimp the stent, under magnification the stent will have the appearance of an octagon. By rotating or indexing the assembly, including the drive disk and stationary disk, and crimping a number of times at a preselected number of degrees N, a more uniformly crimped stent is obtained. For example, in one embodiment the assembly may be rotated 5°, and the stent then crimped. The assembly is then rotated five more degrees, and the stent crimped again, and so on up to 45° rotation in one direction, and 45° rotation in the opposite direction. In this manner, the stent will be uniformly crimped and have the appearance, under magnification, of a substantially perfect cylinder.

The rotational force imparted to the drive disk can take any number of forms, including a lever to apply mechanical force, an electric motor, a hydraulic means, and pneumatic means. Further, the amount of force applied by the apex of each wedge onto the stent and the catheter, can be measured and controlled so that the stent and catheter are not damaged while the stent is being tightly crimped onto the catheter.

In one method of crimping the stent onto the catheter, the stent crimping assembly previously described is provided. Rotational movement is imparted to the drive disk which translates to linear movement to the wedges so that the apexes of the wedges form an opening. A stent, that has been premounted on the distal portion of a catheter, is positioned within the opening provided by the apex of the wedges. Rotational movement is imparted to the drive disk which again translates to linear movement to the wedges so that the apexes of the wedges move linearly toward a closed position and into contact with a stent. The stent is crimped onto the catheter by continuing to apply rotational movement to the drive disk and linear movement to the apexes of the wedges toward a closed position and into further crimping contact with the stent. The amount of force applied to the stent can be determined several ways including by force-measuring sensors on the wedges, by the diameter of the opening of the wedges when the stent is crimped or by determining the distance the lever arm moves. After a predetermined amount of force is applied to crimp the stent, the rotational movement to the drive disk is reversed, so that the apexes of the wedges move in a linear direction toward the open position. The crimped stent and catheter are then removed from the crimping assembly.

In one embodiment, the stent crimping device operates as described to crimp a self-expanding stent onto a mandrel. Typically, self-expanding stents are formed of a nickel-titanium alloy that exhibits shape memory effects, super-elastic effects, or both. The stent can be cooled by dry ice or other similar cooling means and then mounted on the mandrel where it is tightly crimped onto the mandrel where it is tightly crimped onto the mandrel while it is cooled. The stent is then slipped off of the mandrel and inserted into a catheter for subsequent use to repair a vessel. It may be necessary to place the stent crimping assembly in a chamber so that the chamber can be cooled to a temperature below that which martensite forms so that the stent is more malleable and easily crimped onto the mandrel.

In another embodiment of the invention, the device is used to measure the radial force of a stent. The roller bearing is positioned radially outwardly away from the wedges a sufficient distance so that very little force can be transmitted to the wedges. In this configuration, instead of crimping a stent, an expanded or unexpanded stent is placed in the device with the wedges in the open position. The wedges are moved toward the closed position as previously described and into contact with the stent. The radial force of the stent is measured by continuing to move the wedges toward the closed position. The radial force of the stent is measured by using strain gauges, the geometric position of the wedges, or similar means, to measure the radial resistance of the stent as the wedges continue to move toward the closed position.

These and other advantages of the present invention will become more apparent from the following description thereof when taken in conjunction with the following drawings.

BRIEF DESCRIPTION OF THE DRAWINGS

FIG. 5a depicts a front view of the sliding wedge.

FIG. 5b depicts a side view of the sliding wedge.

FIG. 5c depicts a top view of the sliding wedge.

FIG. 11 depicts a rear elevational view of the stent crimping assembly showing different locations for the roller bearing.

DETAILED DESCRIPTION OF THE PREFERRED EMBODIMENTS

Figure 1:
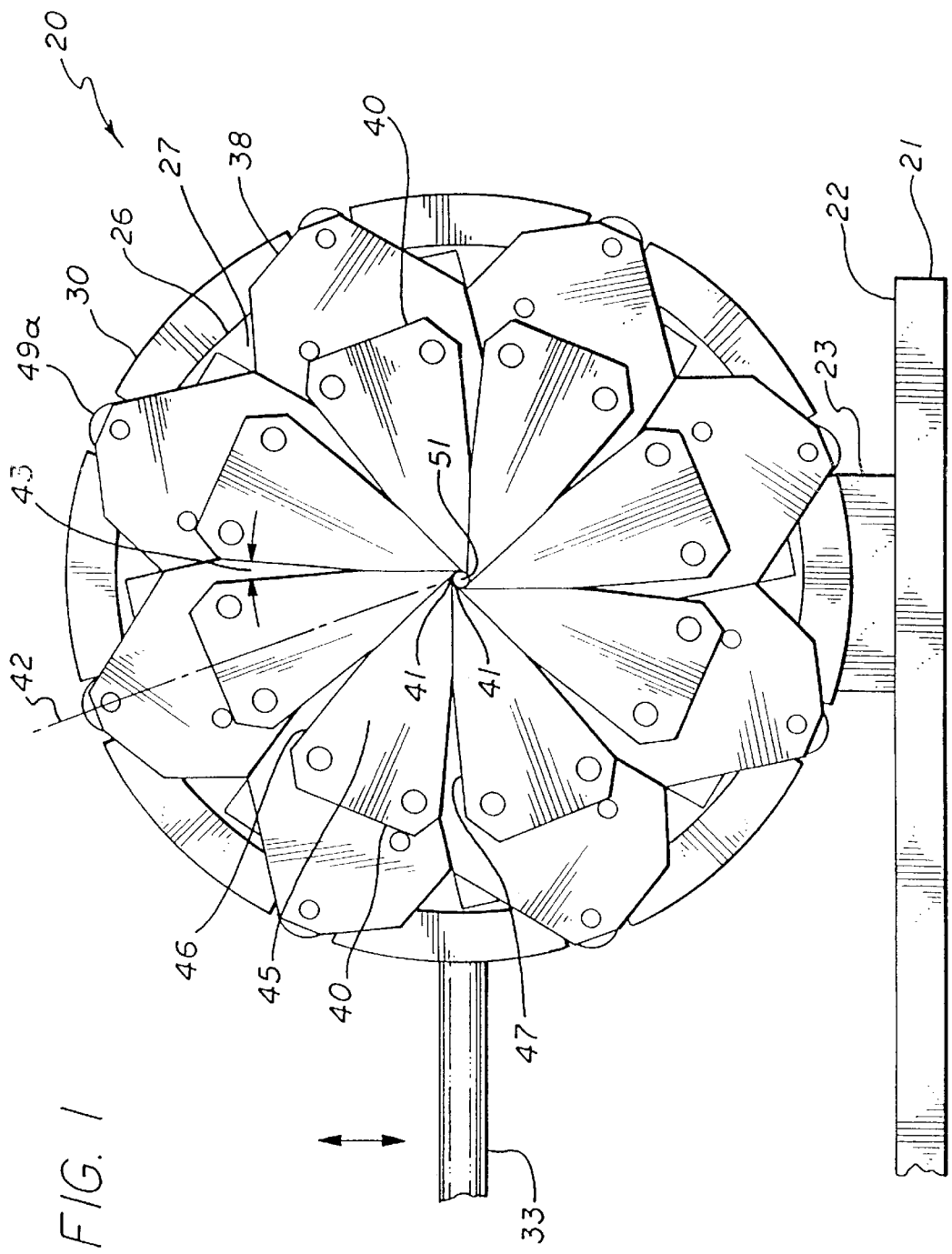
FIG. 1 depicts a front elevational view of the stent crimping assembly.
Figure 2:
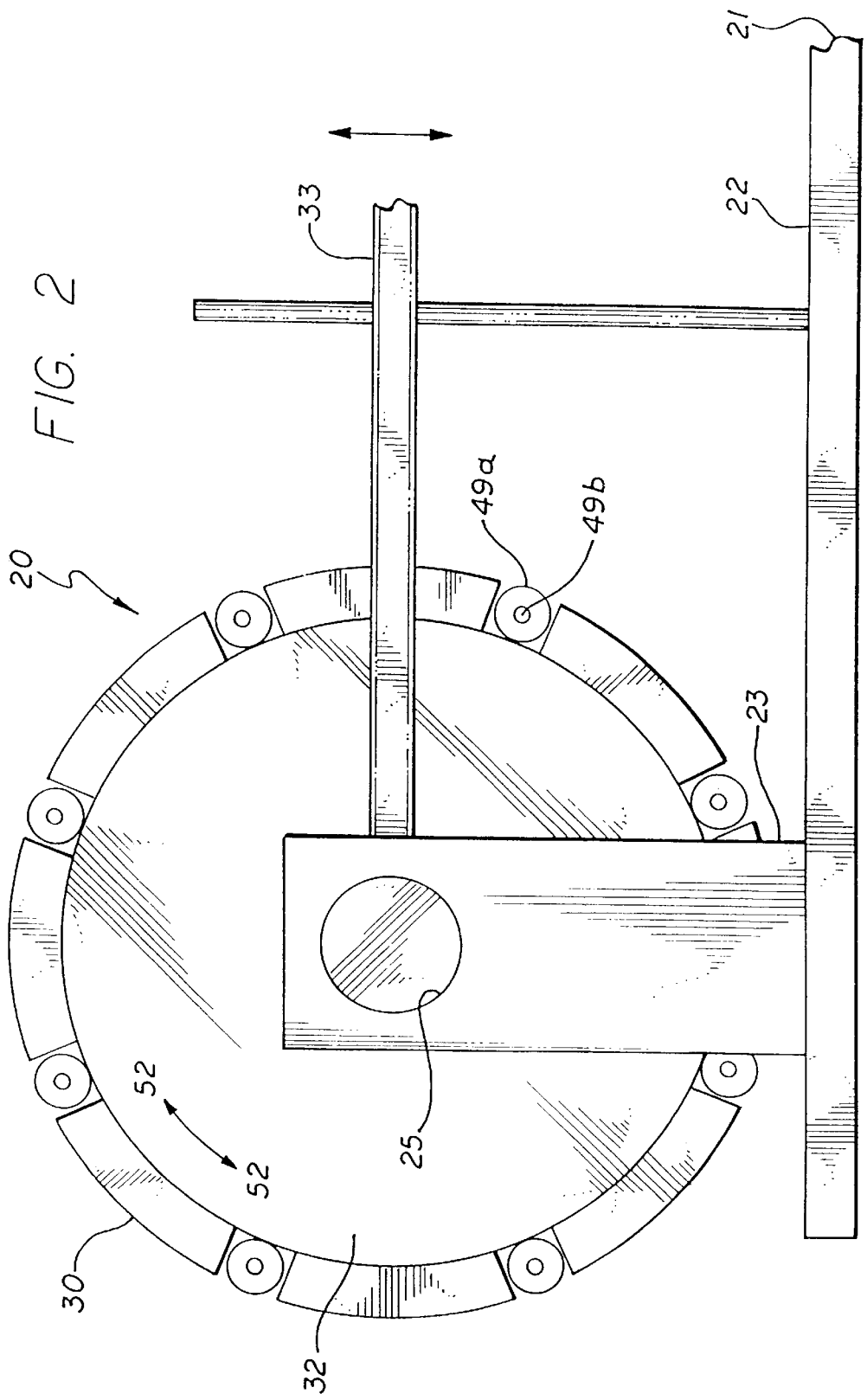
FIG. 2 depicts a rear elevational view of the stent crimping assembly.
Figure 3:
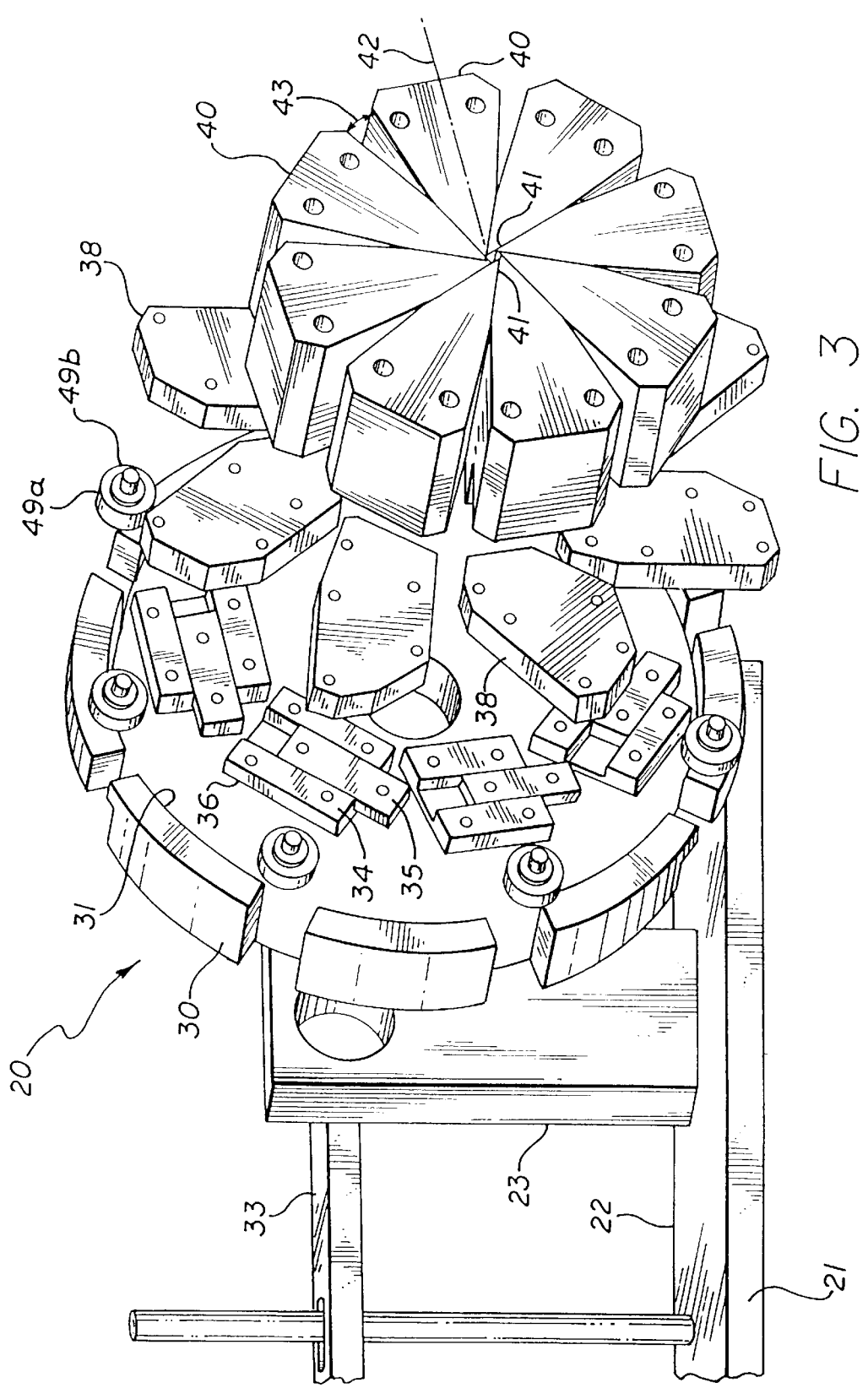
FIG. 3 depicts an exploded perspective view of the stent crimping assembly.

The present invention stent crimping assembly provides for a reliable and uniform crimp of any stent onto a catheter. The stent crimping assembly is capable of crimping almost any size stent, or length of stent, onto the distal portion of a catheter, including stents for coronary arteries and peripheral arteries. The terms crimping and compressing as used herein are meant to be interchangeable and mean that the diameter of the stent is reduced to some degree. Typically, balloon-expandable stents are known by persons having ordinary skill in the art to be "crimped" onto the balloon portion of a catheter while self-expanding stents are compressed onto a mandrel or sheath and then inserted into a catheter. Also, references to "stent crimping assembly" as used herein is not meant to be limiting since the assembly can be used as a measuring device to accurately measure the radial strength of a stent. Thus, for ease of reference, the device has been referred to throughout as a stent crimping assembly, but it also is used to measure the radial strength of a stent. Further, while reference is made herein to crimping or compressing "stents," the invention can be used with any intraluminal device to reduce the diameter or measure radial strength. Thus, the invention is particularly useful with stents, grafts, tubular prostheses, embolic devices, embolic filters, and embolic retrieval devices.

The present invention also can be used to compress a self-expanding stent onto a mandrel or a sheath and then insert the compressed stent into a catheter for subsequent use to repair a vessel. The present invention also can be used to measure the radial force of an expanded or unexpanded stent.

As used herein, the "apex" of the wedges is intended to mean that portion of the wedge that comes into contact with the stent during the crimping or compressing process. Thus, the apex is near the tip of the wedge and along the side of the wedge where the stent will come in contact as shown in FIGS. 6–10.

In keeping with the invention as shown in FIGS. 1–4, the stent crimping assembly 20 is composed of a base 21 on which platform 22 is attached. A vertical support column 23 is attached to and extends upwardly from the base. A pair of shafts that are coaxial to each are attached to the support column and extend at a 90° angle from the support column. A rotating shaft 24 is provided for rotational movement and a stationary shaft 25 is coaxial with and extends within the rotating shaft. A stationary disk 26 is supported by the stationary shaft and it is preferred that the stationary disk have no rotational movement in this embodiment. The stationary disk has a front face 28 and a rear face 29 as can be seen in the drawings. A drive disk 30 is approximately the same diameter as the stationary disk and is mounted on the rotating shaft so that it is adjacent to the stationary disk. The drive disk has a front face and a rear face and is positioned in relation to the stationary disk so that the front face of the drive disk is adjacent to and in relatively close proximity to the rear face 29 of the stationary disk. Rotational movement is imparted to the drive disk by rotating the rotating shaft 24 by any of a number of means. As illustrated in FIGS. 1–4, a lever 33 is attached to the rotating shaft so that as the lever is moved in a vertical position, the shaft is rotated in either a clockwise or counterclockwise direction. Rotating the shaft in turn rotates the drive disk 30 a corresponding number of degrees. It is contemplated that other means are available to impart rotational movement to the rotating shaft, and in turn the drive disk. For example, an electric motor (not shown) can be attached to the rotational shaft to impart rotational movement. Likewise, either hydraulic or pneumatic means may be employed to impart rotational movement to the rotating shaft. Importantly, the amount of rotation to the shaft, and hence rotation of the drive disk, must be controllable in both the clockwise and counterclockwise direction, as will be more fully described herein. References to a "disk" herein are not meant to be limiting and, although the disclosed disks are circular, they can be other shapes without departing from the invention (e.g., square, oval, rectangular). If the drive disk is not circular, however, then the roller bearing should be carried in an arcuate slot (see FIG. 11).

In further keeping with the invention, the linear slider 34 is attached to the face 28 of the stationary disk. The linear slider has a base 35 which is positioned in a carriage 36 so that the base slides within the carriage. The carriage is attached to the stationary disk typically by attachment screws. As will be described more fully herein, it is the purpose of the linear slider to convert the rotational movement of the drive disk to linear movement to the sliding wedges of the invention.

Figure 4:
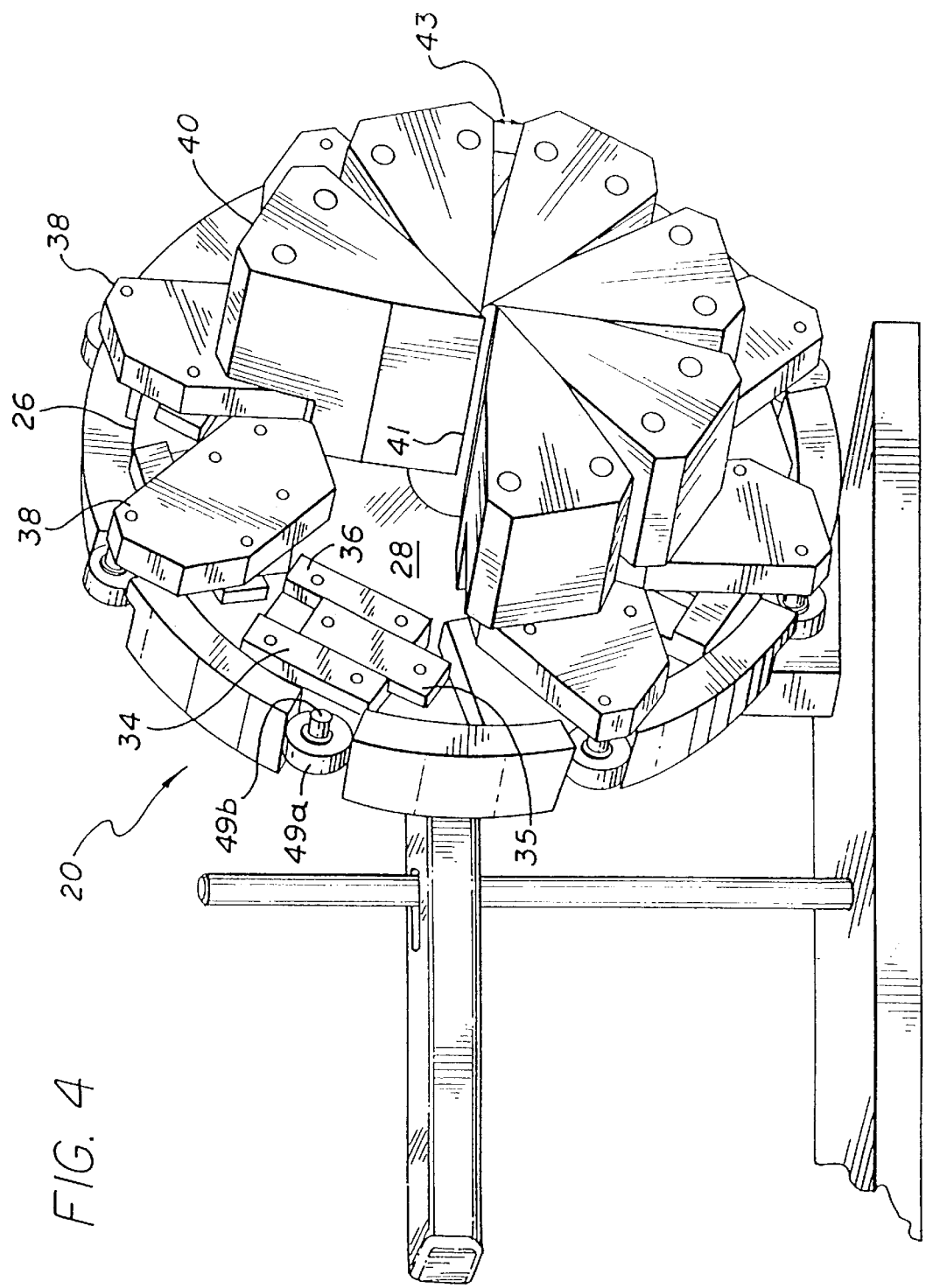
FIG. 4 depicts a partially exploded elevational view of the stent crimping assembly.
Figure 6:
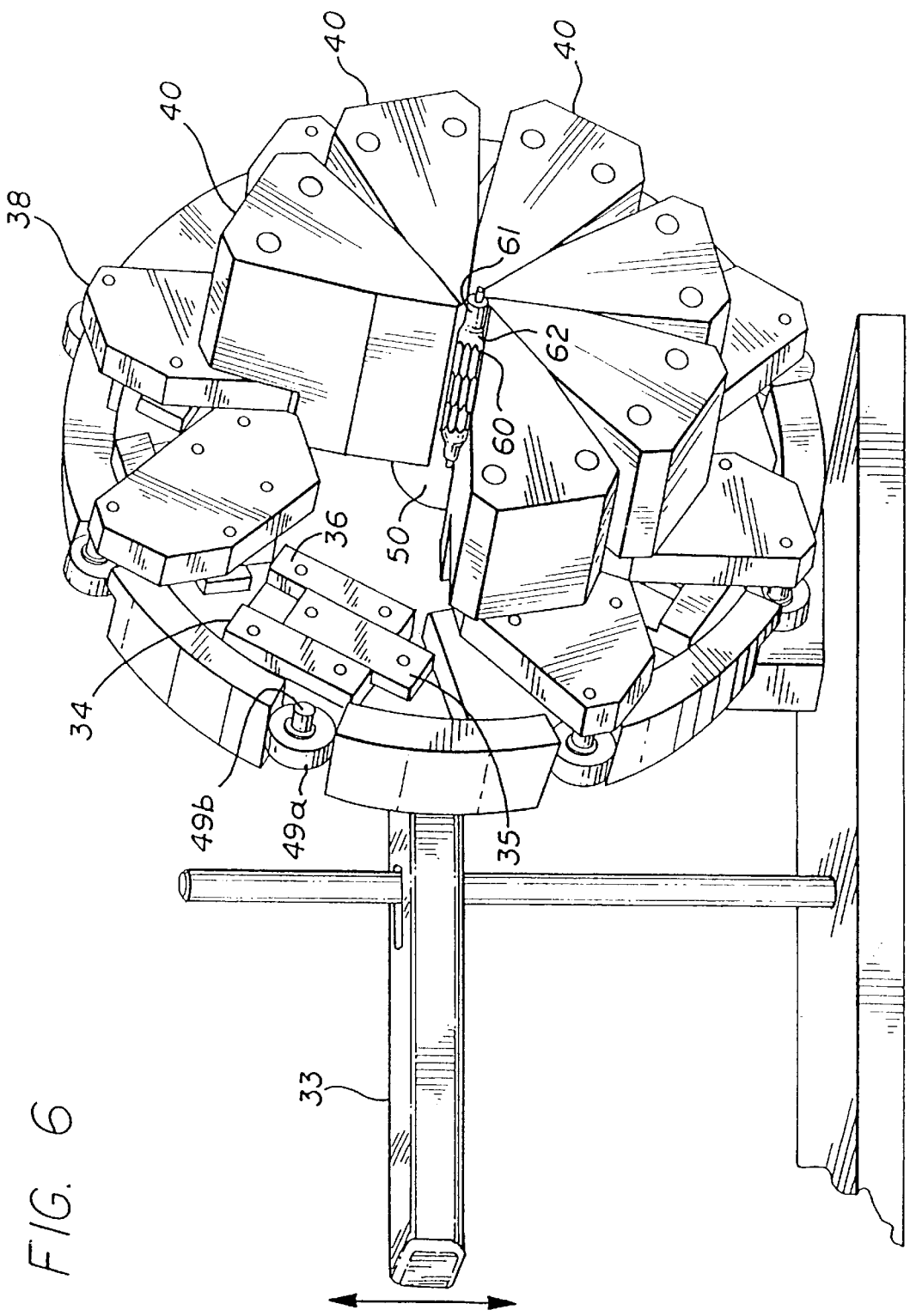
FIG. 6 depicts a perspective view of the stent crimping assembly with a stent premounted on a catheter positioned in the opening of the assembly.
Figure 6A:
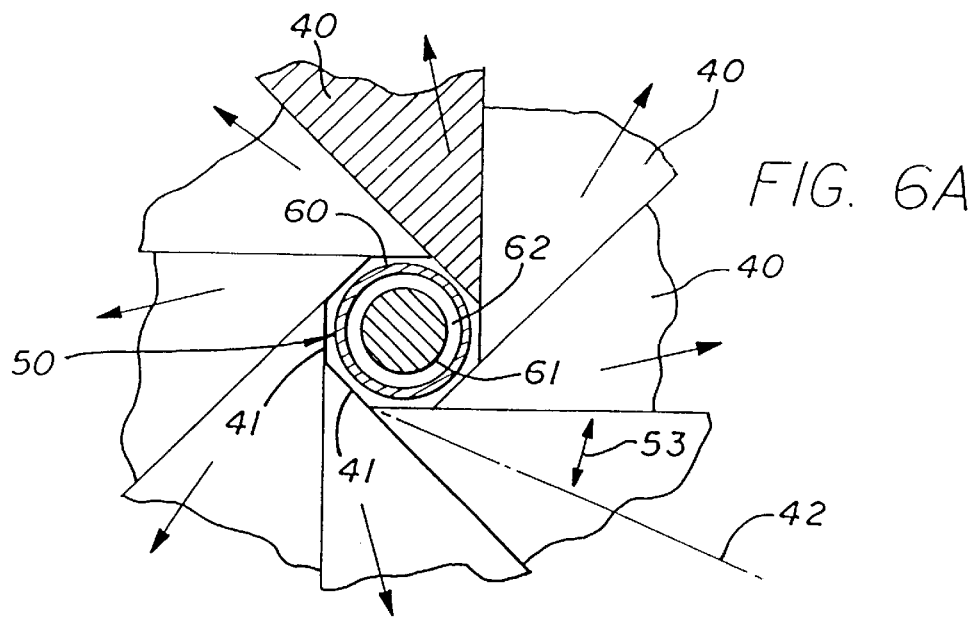
Figure 7A:
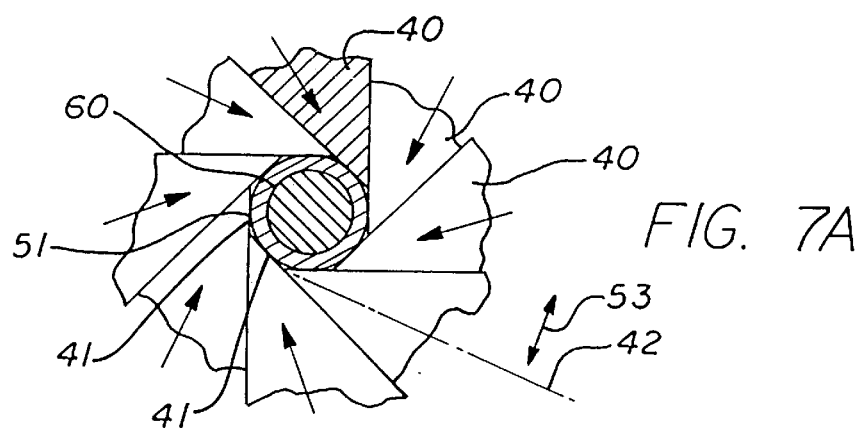
FIG. 7 depicts the stent crimping assembly of FIG. 6 where the wedges have been linearly moved toward the closed position.
Figure 8A:
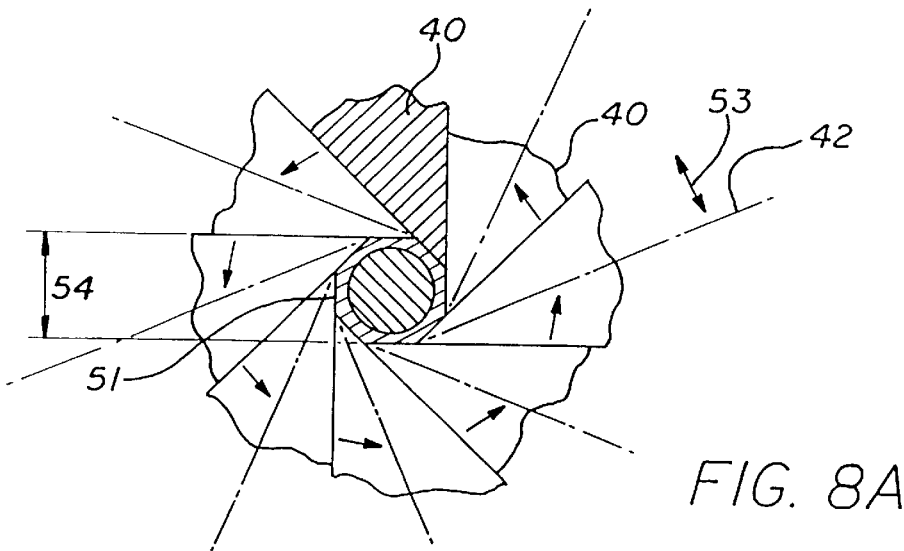
FIG. 8 depicts the stent crimping assembly of FIG. 6 where the wedges have been moved linearly toward the closed position and into crimping engagement with the stent.
Figure 7:
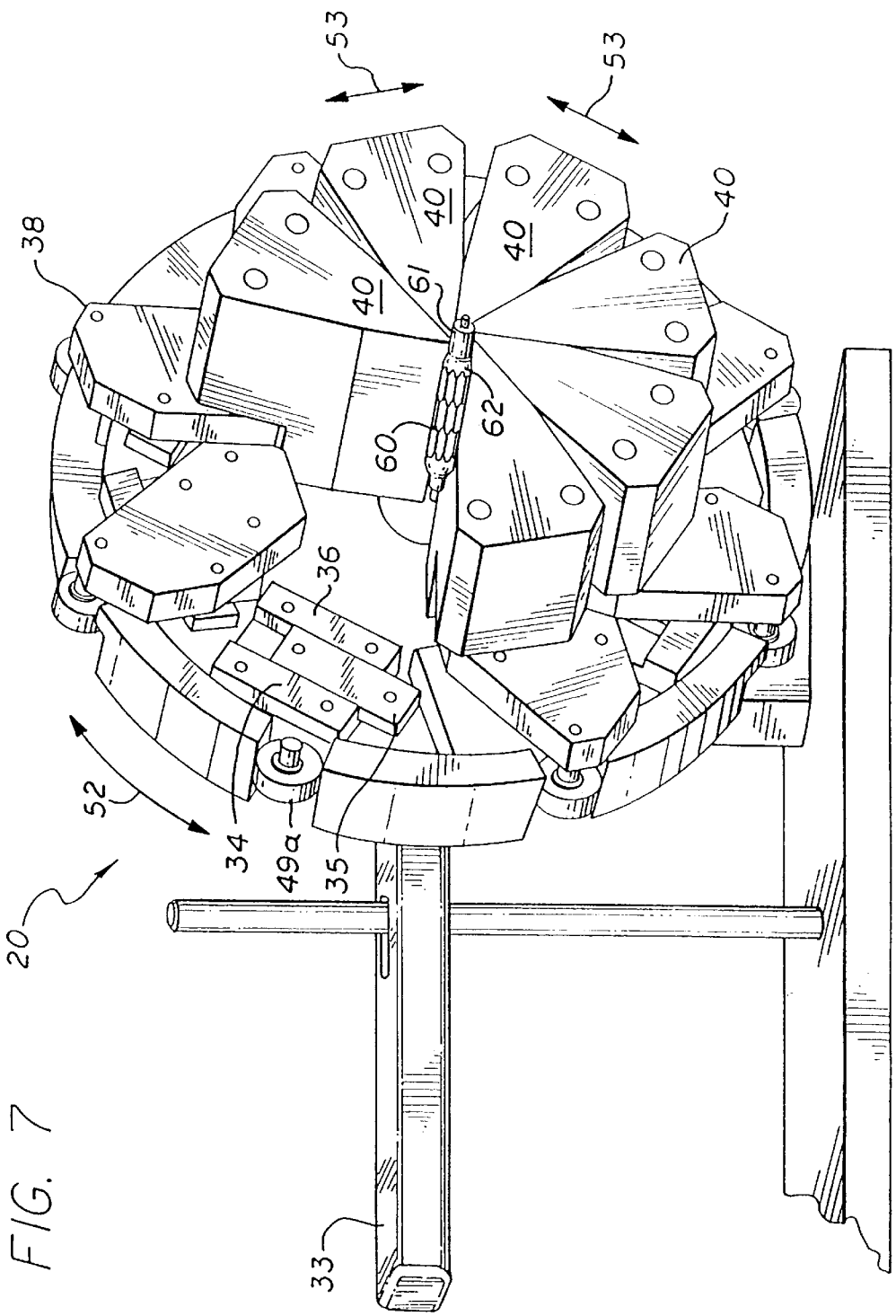
Figure 8:
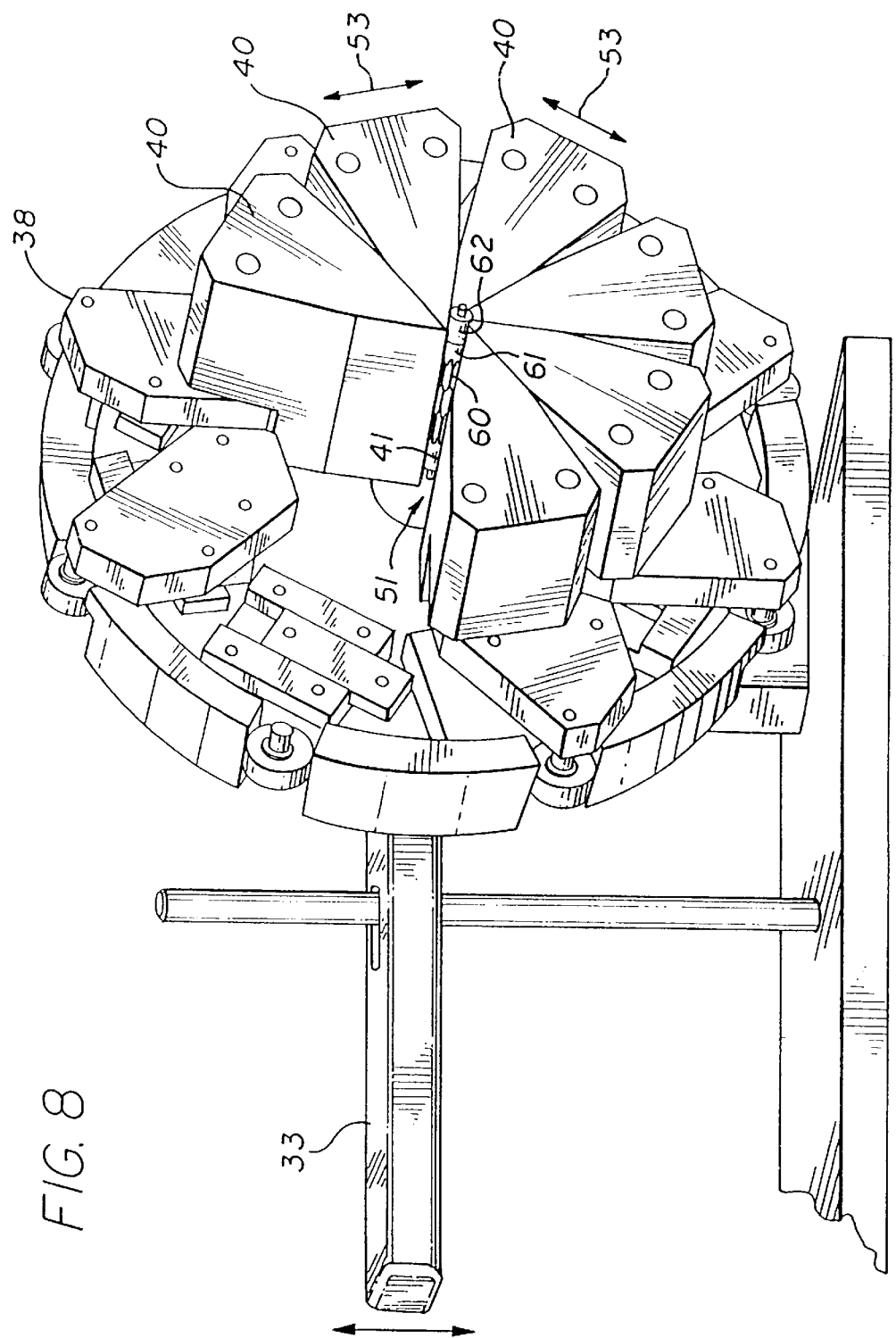
Figure 9:
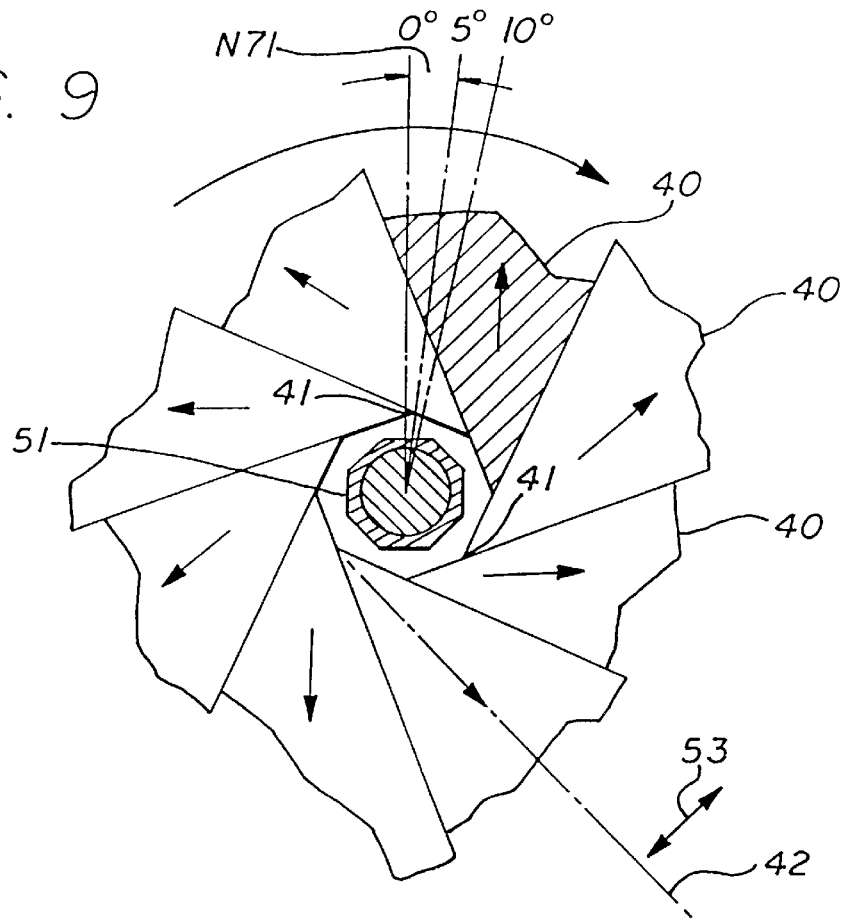
FIG. 9 depicts the stent crimping assembly of FIG. 6 where the wedges have moved linearly toward the open position and the stent, now mounted on the catheter, is withdrawn from the assembly.
Figure 10:
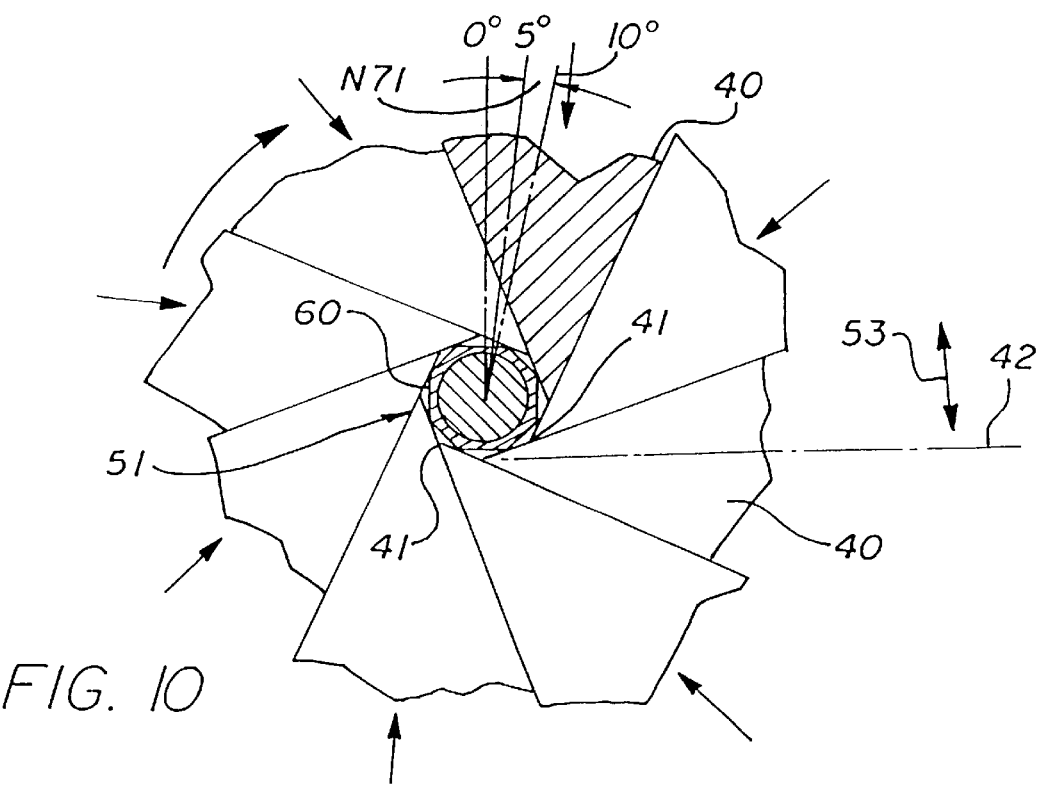
FIG. 10 depicts the stent crimping assembly of FIG. 6 being indexed N degrees for subsequent crimping procedures.

As shown in FIG. 4, a bracket 38 is attached to the linear slider, and more appropriately to the base 35 of the linear slider. The bracket can have essentially any configuration and is intended to be carried linearly by the linear sliding movement of the base 35.

In order to impart a crimping or compressing force on a stent, sliding wedges are provided so that they come into contact with a stent and crimp it onto a catheter. As shown in FIGS. 1–5, and in particular FIGS. 5a–5c, a plurality of wedges 40 are attached to the bracket so that wedges will have the same linear movement as does the bracket, which is attached to the linear slider. Each of the wedges has two sides 46 and 47 which meet to define an apex 41. Those portions of each side that are immediately adjacent apex 41 and which come into contact with the corresponding edges of adjacent wedges, exterior edges 46a and 47a, define an exterior angle, the bisect of which is identified by reference numeral 42. The wedge has a top 45 and a bottom 44 so that the wedge bottom attaches to the bracket 38 by any convenient means, including attachment screws, adhesives, and the like. Bracket 38 can have any shape, and in fact is unnecessary. The bracket is provided as a spacer between the wedges 40 and the linear slider. The wedges in fact could be formed such that the wedge bottom 44 is in the form of the bracket so that the wedges and the brackets are all one piece. As shown in the drawings, it is important that there is a spacing 43 between the wedges so that they can slide relative to one another without an undue amount of friction. The amount of spacing between the wedges is dependent upon several factors, including the number of wedges used in the assembly. Accordingly, the spacing is dependent upon the specific application, keeping in mind that it is important to reduce the amount of friction in the assembly during the crimping operation. As shown more clearly in FIG. 5c, wedge angle alpha 48 is defined by the difference between the taper of edges 46a, 47a immediately adjacent apex and the balance of each side 46, 47 of the wedge. The angle alpha can vary as desired and typically will be greater or lesser depending upon the number of wedges used in the stent crimping assembly. Preferably, the stent crimping assembly will have between three and eight wedges, and more preferably eight wedges are desirable to provide a uniformly crimped stent. The number of wedges used can be increased or decreased depending on the particular application.

In order to impart linear motion to the wedges, a roller 49A and roller arm 49B are attached to the assembly. Specifically, roller arm 49B is attached to the brackets 38 and the roller 49A is in contact with drive disk 30. As rotational movement is imparted to the drive disk, it is also imparted to the roller and the roller arm, which in turn imparts movement to the brackets. Since the brackets are attached to the linear slider 34, the brackets, and hence the wedges, can only move in a linear direction. The roller minimizes any friction between the rotational movement of the drive disk and the linear movement imparted to the brackets and the wedges. Other means are available to connect the brackets to the drive disk including a member without a roller, however, it is important to reduce the friction so that the assembly operates smoothly.

As the brackets and wedges move in a linear fashion, the linear movement is perpendicular to the bisect 42 of the exterior angle defined by edges 46a and 47a of each wedge. Accordingly, the apex of each wedge moves linearly in a direction that also is perpendicular such bisect of the wedge edges.

The stent crimping assembly has an open position 50 and a closed position 51 as shown in FIGS. 6–10. As rotational movement 52 is imparted to the drive disk, the apexes of the wedges will move linearly toward the open position, and when the drive disk is rotated in the opposite direction, the apexes of the wedges will move toward the closed position. The linear movement 53 defined by the apexes of the wedges creates a parallel gap 54 with respect to wedges that are 180° opposite to each other on the stationary disk. In other words, the apices of the wedges that are 180° opposite of each other move in a linear fashion and define the parallel gap.

One method for crimping the stent onto a catheter includes multiple applications of crimping force by the sliding wedges onto the stent. A stent 60 is first premounted onto a catheter 61, preferably near the distal end thereof. Preferably, the catheter will have an inflatable expandable member 62, generally an inflatable balloon, upon which the stent is first premounted. The stent and the balloon portion of the catheter are positioned within the stent crimping assembly 20 when the wedges are in the open position 50. The drive disk is rotated as previously described to impart rotational movement which is transmitted to the roller 49A. The rotational movement is imparted to the brackets and wedges, which is converted to linear movement by the linear slider 34. As the wedges move linearly toward the closed position 51, the apices of the wedges come into contact with the stent. As further rotational movement is imparted, the wedges continue to move in a linear direction and continue to move toward the closed position thereby imparting crimping force on the stent. Preferably, eight sliding wedges are used to impart crimping force on the stent so that when initially crimped the stent will have the appearance of an octagon when viewed under magnification. In order to form a more perfect cylinder on the stent, it may be desirable to repeatedly crimp the stent by slightly rotating the stent and catheter a few degrees and then applying further crimping force. The opening and closing of the sliding wedges in this manner will provide a stent that is tightly crimped onto the catheter and will have the appearance of a substantially perfect cylinder when viewed under magnification.

It may be desirable to measure or limit the amount of force imparted by the wedges onto the stent, and this can be accomplished by any number of means including providing mechanical or electrical stopping switches which limit the closing position of the wedges. By limiting how far the wedges can close, the amount of force also will be limited. The geometric position of the wedges also can indicate how much force is being applied to the stent. Strain gauges also can be attached to the wedges to measure the amount of force being applied to the stent and catheter and can be controlled and monitored to limit the amount of crimping force applied to the stent.

In an alternative embodiment, the drive disk 30 and the stationary disk 26 can be indexed a preselected number of degrees N 71. In this embodiment, the stent and catheter are held stationary within the opening of the stent crimping assembly. The stent is crimped in the manner described, and then the stationary disk and the drive disk are rotated N number of degrees form a 0° position and crimping force is again applied. This procedure is repeated each time the stationary disk and the drive disk are indexed N number of degrees. As an example, the stationary disk and drive disk can be indexed starting from a 0° position every 5° up to 45°, and at every 5° position, the stent is crimped. The stationary disk and drive disk are then moved back to the 0° position and rotated in the opposite direction in 5° increments for 45°, and the stent is crimped at each 5° increment. By crimping the stent multiple times at various degrees along the cylinder, the stent is more uniformly and tightly crimped onto the balloon portion of the catheter so that under magnification it will appear as a substantially perfect cylinder.

In an alternative embodiment of the invention, the stent assembly can be used to measure the radial force of a balloon-expandable or a self-expanding stent. In this embodiment, the roller-bearing 49a, as shown in FIG. 11, would be moved radially outwardly away from the wedges 40. The farther the rolling bearing is from the apex of the wedges, the less force the wedges apply to the stent. Thus, the roller bearing can be positioned so that as the wedges are moved toward the closed position 51 with an unexpanded or expanded stent positioned within the opening formed by the wedges, the radial force of the stent can be measured by the assembly. As the wedges continue to move toward the closed position, they will have a tendency to crush the stent and in so doing the resistance to crushing is measurable, and is determinative of the radial strength of the stent. Different stent patterns will have different radial strengths that can be quantified and measured by the present invention in the manner described. Again, an important feature of being able to measure accurately the radial strength of the stent, the rollers provide a near frictionless movement along with the near frictionless movement of the wedges, which all contribute to an accurate measurement of the radial strength of the stent. Likewise, moving the roller bearing 49a radially closer to the apex of the wedges, as shown in phantom in FIG. 11, results in a greater force applied to the wedges and hence the stent. An arcuate slot 80 is provided for the roller bearing to travel in.

The stent crimping assembly may be formed of plastic and metal parts, however, either all plastic or all metal, or a combination of both, is desirable. For example, both the stationary disk 26 and drive disk 30 can be formed of a polymer including a hard plastic that is machinable. The wedges 40 and brackets 38 also can be formed of a polymer that is machineable so that precise tolerances can be machined into the wedge angle 48 to insure that the wedges move relative to one another without substantial friction. The rotating and stationary shaft can be formed of a conventional shaft material and all attachments can be in the form of metal screws, adhesives or any other conventional attachment means.

In a preferred embodiment, most of the parts of the stent crimping assembly are made from machined polymers, however, the present invention is also well suited to be made from surgical steel, aluminum, or other metals so that it can be used multiple times.

Other modifications can be made to the present invention without departing from the scope thereof. The specific dimensions, procedural steps, and materials of construction are provided as examples, and substitutes are readily contemplated which do not depart from the invention.

What is claimed:

1. An assembly for reducing the diameter of an intraluminal device, comprising:
   a plurality of wedges, each wedge being spaced substantially equidistant from an adjacent wedge, wherein the spacing between wedges is uniform, each wedge having exterior edges that define an angle, such angle having a bisect;
   each wedge being configured for movement in a direction substantially perpendicular to said bisect of said angle defined by said exterior edges for movement into and out of contact with the intraluminal device, wherein the wedges are associated with a stationary disk and a drive disk configured for rotational movement relative to the stationary disk, each wedge being attached to a linear slider mounted on the stationary disk, whereby, as the drive disk is rotated, the apex of the wedges move in a direction that is perpendicular to said bisect and as the apex of each wedge continues to move linearly , the apexes of the wedges move from an open position toward a closed position until the apexes come into contact with the intraluminal device.

2. The assembly of claim 1, wherein the drive disk has a closed rotational position where all of the apexes of the wedges form an opening having a diameter corresponding to the diameter of the crimped intraluminal device.

3. The assembly of claim 1, wherein the drive disk has an open rotational position where all of the apexes of the wedges are spaced apart.

4. The assembly of claim 1, wherein each wedge has a first side and a second side.

5. The assembly of claim 1, wherein a parallel gap is defined by the first side of the first wedge and the first side of the second wedge when the drive disk is in an open rotational position.

6. The assembly of claim 1, wherein the linear slider includes a carriage and a base.

7. The assembly of claim 6, wherein the carriage is attached to the stationary disk.

8. The assembly of claim 6, wherein the base is slidably mounted in the carriage.

9. The assembly of claim 6, wherein the base is attached to a wedge.

10. The assembly of claim 1, wherein a roller bearing transmits rotational movement from the drive disk to the wedge.

11. The assembly of claim 1, wherein the rotational movement translates to linear movement by the linear slider attached to the wedge.

12. The assembly of claim 1, wherein the linear movement translates to the apex of each wedge so that the apex travels linearly in a direction perpendicular to said bisect of said angle defined by the exterior edges of the wedge.

13. The assembly of claim 1, wherein the drive disk and the stationary disk are rotated a preselected number of degrees N and the intraluminal device diameter is reduced.

14. The assembly of claim 13, wherein the drive disk and the stationary disk are repeatedly rotated N degrees and the intraluminal device diameter is further reduced at each N degrees position.

15. The assembly of claim 14, wherein the number of degrees of rotation N is variable from about 1° to about 20°.

16. The assembly of claim 13, wherein the number of degrees of rotation N is 5°.

17. The assembly of claim 13, wherein the rotation of the drive disk and the stationary disk in one direction only.

18. The assembly of claim 13, wherein the drive disk and the stationary disk rotate in either direction.

19. An assembly for crimping an intraluminal device onto a catheter, comprising:
    a stationary disk having a front face and a rear face;
    a drive disk configured for rotational movement relative to the stationary disk and having a front face and a rear face;
    a plurality of linear sliders attached to the front face of the stationary disk;
    a plurality of wedges, each wedge having an apex and having exterior edges that define an angle, such angle having a bisect;
    each wedge being spaced substantially equidistant from an adjacent wedge, wherein the spacing between wedges is uniform, and each wedge being attached to a linear slider and to the drive disk;
    whereby as the drive disk is rotated, the apex of the wedges move in a direction that is perpendicular to said bisect and as the apex of each wedge continues to move linearly, the apexes of the wedges moving from an open position toward a closed position until the apexes come into crimping contact with the intraluminal device so that the intraluminal device is tightly crimped onto the catheter.

20. The assembly of claim 19, wherein at least three wedges are used for crimping the intraluminal device onto the catheter.

21. The assembly of claim 19, wherein eight wedges are used to crimp the intraluminal device onto the catheter.

22. The assembly of claim 19, wherein a plurality of brackets are positioned between the plurality of wedges and the plurality of linear sliders, the brackets being attached to the wedges and to the linear sliders.

23. The assembly of claim 19, wherein the spacing between wedges is predetermined.

24. The assembly of claim 19, wherein the spacing between wedges provides substantially frictionless movement among the wedges.

25. The assembly of claim 19, wherein the drive disk has a closed rotational position where all of the apexes of the wedges form an opening having a diameter corresponding substantially to the diameter of the crimped intraluminal device.

26. The assembly of claim 19, wherein the drive disk has an open rotational position where all of the apexes of the wedges are spaced apart.

27. The assembly of claim 19, wherein each wedge has a first side and a second side.

28. The assembly of claim 27, wherein the first side of a first wedge is substantially parallel to a first side of a second edge and positioned 180° on the drive disk from the first wedge.

29. The assembly of claim 28, wherein a parallel gap is defined by the first side of the first wedge and the first side of the second wedge when the drive disk is in an open rotational position.

30. The assembly of claim 19, wherein the linear slider includes a carriage and a base.

31. The assembly of claim 30, wherein the carriage is attached to the stationary disk.

32. The assembly of claim 30, wherein the base is slidably mounted in the carriage.

33. The assembly of claim 30, wherein the base is attached to a wedge.

34. The assembly of claim 19, wherein a roller bearing transmits rotational movement from the drive disk to the bracket and the wedge.

35. The assembly of claim 34, wherein the rotational movement translates to linear movement by the linear slider attached to the bracket and to the wedge.

36. The assembly of claim 35, wherein the linear movement translates to the apex of each wedge so that the apex travels linearly in a direction perpendicular to said bisect of said exterior edges of the wedge.

37. The assembly of claim 19, wherein the drive disk and the stationary disk are rotated a preselected number of degrees N and the intraluminal device diameter is reduced.

38. The assembly of claim 37, wherein the drive disk and the stationary disk are repeatedly rotated N degrees and the intraluminal device diameter is further reduced at each N degrees position.

39. The assembly of claim 38, wherein the number of degrees of rotation N is variable from about 1° to about 20°.

40. The assembly of claim 37, wherein the number of degrees of rotation N is 5°.

41. The assembly of claim 37, wherein the rotation of the drive disk and the stationary disk in one direction only.

42. The assembly of claim 37, wherein the drive disk and the stationary disk rotate in either direction.

43. The assembly of claim 19, wherein the rotational force imparted to the drive disk is mechanical.

44. The assembly of claim 43, wherein the mechanical force is applied by a lever attached to a shaft and which is associated with the drive disk.

45. The assembly of claim 19, wherein the rotational force is imparted to the drive disk hydraulically.

46. The assembly of claim 19, wherein the rotational force is imparted to the drive disk pneumatically.

47. The assembly of claim 19, wherein the rotational force is imparted to the drive disk electrically.

48. The assembly of claim 47, wherein the electrical force is derived from an electrical motor associated with the drive disk.

49. The assembly of claim 19, wherein rotation of the drive disk from an open to a closed position is limited.

50. The assembly of claim 49, wherein the rotational limits are controlled by mechanical stop.

51. The assembly of claim 49, wherein the rotational limits are controlled by electronic switches.

52. A method for compressing an intraluminal device onto a catheter, a mandrel or a sheath, comprising:
    providing an intraluminal device compressing assembly having a drive disk providing for rotational movement and a stationary disk, both disks being mounted on a base, a plurality of wedges attached to a corresponding plurality of linear sliders on the stationary disk, each wedge being spaced substantially equidistant from an adjacent wedge, wherein the spacing between wedges is uniform, each of the wedges having an apex and exterior edges that define an angle, said angle having a bisect;

imparting rotational movement to the drive disk which translates to linear movement to the wedges so that the apexes of the wedges form an opening and wherein the apexes of the wedges move in a linear direction that is perpendicular to said bisect of each corresponding wedge;

providing an intraluminal device pre-mounted on a catheter and positioning the intraluminal device within the opening;

imparting rotational movement to the drive disk which translates to linear movement to the wedges so that the apexes of the wedges move linearly toward a closed position and into contact with the intraluminal device;

compressing the intraluminal device onto the catheter, mandrel or sheath by continuing to move the apexes of the wedges in a linear direction toward the closed position and into contact with the intraluminal device;

imparting rotational movement to the drive disk which translates to linear motion to move the apexes of the wedges in a linear direction toward the open position; and removing the intraluminal device and catheter or mandrel or sheath from the intraluminal device compressing assembly.

53. An assembly for crimping an intraluminal device onto a catheter, comprising:

a stationary disk having a front face and a rear face;

means for providing rotational movement relative to the stationary disk;

a plurality of linear sliders attached to the front face of the stationary disk;

a plurality of wedges, each wedge being spaced substantially equidistant from an adjacent wedge, wherein the spacing between wedges is uniform, each wedge having an apex and exterior edges defining an angle, said angle having bisect;

each wedge being attached to a linear slider and to the means for providing rotational movement;

whereby as rotational movement is provided, the apex of the wedges move in a direction that is perpendicular to said bisect and as the apex of each wedge continues to move linearly, the apexes of the wedges moving from an open position toward a closed position until the apexes come into crimping contact with the intraluminal device so that the intraluminal device is tightly crimped onto the catheter.

54. The assembly of claim 53, wherein the means for providing rotational movement includes a drive disk.

55. An assembly for measuring the radial strength of a intraluminal device, comprising:

a stationary disk having a front face and a rear face;

a drive disk configured for rotational movement relative to the stationary disk and having a front face and a rear face;

a plurality of linear sliders attached to the front face of the stationary disk;

a plurality of wedges, each wedge having an apex and having exterior edges that define an angle, said angle having a bisect;

each wedge being positioned equidistant from an adjacent wedge, wherein the spacing between wedges is uniform, and each wedge being attached to a linear slider and to the drive disk;

whereby as the drive disk is rotated, the apex of the wedges move in a direction that is perpendicular to said bisect and as the apex of each wedge continues to move linearly, the apexes of the wedges moving from an open position toward a closed position until the apexes come into crimping contact with the intraluminal device so that the radial strength of the intraluminal device can be measured.

56. The assembly of claim 55, wherein at least three wedges are used for contacting the intraluminal device.

57. The assembly of claim 55, wherein eight wedges are used for contacting the intraluminal device.

58. The assembly of claim 55, wherein a plurality of brackets are positioned between the plurality of wedges and the plurality of linear sliders, the brackets being attached to the wedges and to the linear sliders.

59. The assembly of claim 55, wherein the spacing between wedges is predetermined.

60. The assembly of claim 55, wherein the spacing between wedges provides substantially frictionless movement among the wedges.

61. The assembly of claim 55, wherein the drive disk has a closed rotational position where all of the apexes of the wedges form an opening having a diameter corresponding to an unexpanded diameter of the intraluminal device.

62. The assembly of claim 55, wherein the drive disk has an open rotational position where all of the apexes of the wedges are spaced apart.

63. The assembly of claim 55, wherein each wedge has a first side and a second side.

64. The assembly of claim 63, wherein the first side of a first wedge is substantially parallel to a first side of a second edge and positioned 180° on the drive disk from the first wedge.

65. The assembly of claim 64, wherein a parallel gap is defined by the first side of the first wedge and the first side of the second wedge when the drive disk is in an open rotational position.

66. The assembly of claim 55, wherein the linear slider includes a carriage and a base.

67. The assembly of claim 66, wherein the carriage is attached to the stationary disk.

68. The assembly of claim 66, wherein the base is slidably mounted in the carriage.

69. The assembly of claim 66, wherein the base is attached to a wedge.

70. The assembly of claim 55, wherein a roller bearing transmits rotational movement from the drive disk to the bracket and the wedge.

71. The assembly of claim 70, wherein the rotational movement translates to linear movement by the linear slider attached to the bracket and to the wedge.

72. The assembly of claim 55, wherein the linear movement translates to the apex of each wedge so that the apex travels linearly in a direction perpendicular to said bisect of said angle defined by said exterior edges.

73. The assembly of claim 55, wherein the radial strength of the intraluminal device is determined by the geometric position of wedges.

* * * * *